United States Patent [19]

Harkrader et al.

[11] Patent Number: 5,133,981
[45] Date of Patent: Jul. 28, 1992

[54] PURIFICATION OF BENZOPHENANTHRIDINE ALKALOIDS EXTRACTS FROM ALKALOID EXTRACTS

[75] Inventors: Ronald J. Harkrader, Louisville; Richard R. Jones, Fort Collins, both of Colo.

[73] Assignee: Atrix Laboratories, Inc., Fort Collins, Colo.

[21] Appl. No.: 439,096

[22] Filed: Nov. 17, 1989

[51] Int. Cl.⁵ .................... A61K 35/78; A01N 43/42
[52] U.S. Cl. ................... 424/195.1; 514/279
[58] Field of Search ............. 424/195.1; 514/279

[56] References Cited

U.S. PATENT DOCUMENTS

| | | | |
|---|---|---|---|
| 3,865,830 | 2/1975 | Turkevich | 260/283 P |
| 4,145,412 | 3/1979 | Ladanyi | 424/58 |
| 4,376,115 | 3/1983 | McCrorey | 424/145 |
| 4,599,228 | 7/1986 | Ladanyi | 424/52 |
| 4,737,503 | 4/1988 | Sakamoto | 514/279 |
| 4,767,861 | 8/1988 | Boulware | 546/41 |
| 4,769,452 | 9/1988 | Boulware | 540/476 |
| 4,816,462 | 3/1989 | Nowicky | 514/279 |
| 4,818,533 | 4/1989 | Boulware | 424/195.1 |

FOREIGN PATENT DOCUMENTS

| | | |
|---|---|---|
| 2856577 | 5/1980 | Fed. Rep. of Germany . |
| 2901406 | 7/1980 | Fed. Rep. of Germany . |
| 230387 | 9/1967 | U.S.S.R. . |
| 2042336 | 9/1980 | United Kingdom . |

OTHER PUBLICATIONS

Steinmetz E. F. Codex Vegetabilis 1957, #277, 1018.

*Primary Examiner*—John W. Rollins
*Assistant Examiner*—Ralph Gitomer
*Attorney, Agent, or Firm*—Merchant, Gould, Smith, Edell, Welter & Schmidt

[57] ABSTRACT

A method for separating and purifying individual benzophenanthridine alkaloids from alkaloid extracts by using the pH differences in formation of their respective alkanolamine or base forms and iminium ions. The insoluble base form of the alkaloid is collected as a precipitate and dissolved in an organic solvent and converted to the insoluble iminium ion form with a mineral or organic acid.

10 Claims, 2 Drawing Sheets

PURIFICATION OF BENZOPHENANTHRIDINE ALKALOIDS EXTRACTS FROM ALKALOID EXTRACTS

BACKGROUND OF THE INVENTION

Sources of benzophenanthridine alkaloids include five plant families: Papaveraceae, Fumariaceae, Rutaceae, Capifoliaceace, and Meliaceae. Two of the most important sources of benzophenanthridine alkaloids are found in the Papaveraceae family. These plant species are *Sanguinaria canadensis* L. (bloodroot) and Macleaya spp. *Sanguinaria canadensis* L. is commonly known as bloodroot puccoon, teterwort and is a perennial plant native to North America. The plant and its extracts have been used as a folk remedy for treating asthma, bronchitis, dysentery, ringworm and other ailments. The rhizome of the plant has been used as an expectorant in cough syrups and in homeopathic medicine.

Recently Sanguinaria extract derived from the rhizome has been used as an antiplaque and gingivitis agent as shown in U.S. Pat. No. 4,145,412 with zinc chloride, and as an antimicrobial agent in U.S. Pat. No. 4,406,881 and USSR Patent No. 230,387. The following patents describe the use of benzophenanthridine alkaloid extracts in medical ailments: U.S. Pat. No. 4,376,115; U.K. Patent No. 2,042,336; German Patent No. 2,907,406; and Belgian Patent No. 888,843.

As a result of their activity in treating medical conditions it has become increasingly important to develop methods for extraction of these benzophenanthridine alkaloids from plant biomass. It has also become important to develop commercial methods for purifying and separating these benzophenanthridine alkaloids from each other. The benzophenanthridine alkaloids of interest are sanguinarine, chelerythrine, sanguilutine, chelilutine, chelirubine and sanguirubine. In the past, methods for the separation of these alkaloids from each other included column chromatography and thin layer chromatography. However, these methods do not lend themselves to production of commercial quantities of these alkaloids.

The prior art for extracting the benzophenanthridine alkaloids from plant biomass include the extraction of cut or ground bloodroot with methanol at elevated temperatures, filtering the liquid extract, evaporating the extract to dryness, dissolving the dried extract in chloroform, adjusting the pH of the chloroform solution with acid such as hydrochloric acid, collecting the filtered extract, and drying of the extract. This procedure is disclosed in U.S. Pat. No. 4, 145,412, incorporated herein by reference. Other patents for the extraction of benzophenanthridine alkaloids from plant biomass include USSR Patent No. 495,331 for extracting *Chelidonium majus* from benzophenanthridine alkaloids.

German Patent No. 2,856,577 discloses a method of benzophenanthridine alkaloid extraction by treating chopped plant materials with an ammonia solution and subsequent extraction with trichloromethane solution. Sulfuric acid is added and the solvent is distilled off. The residue is basified with ammonia to precipitate the alkaloid free bases. The bases are collected.

U.S. Pat. No. 4,818,533 describes the extract of plant material for benzophenanthridine alkaloids using a pH 8.5 solution of water and co-solvent such as methylene chloride to dissolve the alkaloid. The methylene chloride solution is washed with acidified water and the benzophenanthridine alkaloids are precipitated as the acid salt.

Other U.S. patents describing the extraction of benzophenanthridine alkaloids from a plant biomass include: 4,767,861 and 4,769,452.

SUMMARY OF THE INVENTION

The invention is directed to the separation and purification of the individual benzophenanthridine alkaloids from each other on a commercial scale in an economical manner. It is an object of this invention to provide a high-purity benzophenanthridine alkaloid with only traces of other alkaloids present. In particular this invention provides processes for purifying sanguinarine from the other benzophenanthridine alkaloids, chelerythrine, sanguilutine, chelilutine, sanguirubine, chelirubine, dihydrosanguinarine and norsanguinarine. The invention relates to a method for separating and purifying benzophenanthridine alkaloids from an alkaloid extract derived from plants. It is based upon the formation of the water and alcohol insoluble base forms of the alkaloids at selective pH values. Collection of the precipitate is followed by dissolution of the base form of alkaloid in an organic solvent. The addition of a mineral or organic acid results in crystallization of the selected benzophenanthridine alkaloid in high purity with only traces of the other benzophenanthridine alkaloids present.

DETAILED DESCRIPTION OF THE INVENTION

The aqueous pH values for the complete conversion of these alkaloids to the base form is shown in Table 1.

TABLE 1

|  | pH of Base Form |
|---|---|
| Sanguinarine | 8.0 |
| Chelirubine | 7.7 |
| Sanguirubine | 7.9 |
| Chelerythrine | 9.0 |
| Chelilutine | 8.7 |
| Sanguilutine | 8.8 |

The alkaloids, sanguinarine, sanguirubine and chelirubine, can be selectively converted to the base form with only traces (<1.0%) of the other three benzophenanthridine alkaloids. This base formation for sanguinarine begins at pH 5.5. (R. Jones *Journal Natural Products* 49, 1986)

The present invention process requires the dissolution of the isolated alkaloid extract into a solvent such as methanol, ethanol or water. The pH is adjusted to pH 5.5-7.0 with any available base such as sodium carbonate, sodium bicarbonate, ammonium hydroxide, sodium hydroxide, potassium hydroxide, sodium hydride and the like. This pH adjustment selectively converts sanguinarine to the free base or pseudobase which is insoluble in alcohol and water. Chelerythrine, chelilutine and sanguilutine remain soluble. The free base is collected by filtration and washed with alcohol or water to remove any trapped soluble alkaloid. The alkaloid precipitate is dried. The precipitate is suspended in an alcohol such as methanol, ethanol, or the like and acidified with a mineral acid such as hydrochloric acid, sulfuric acid, or nitric acid and allowed to recrystallize as the mineral acid salt.

Alternatively, the free base form can be resuspended in an alcohol and crystallized in the iminium ion form as the organic acid salt using gluconic acid, lactic acid, benzoic acid, palmitic acid and the like. The acid precipitated benzophenanthridine alkaloid is collected and dried. This procedure results in recovery of sanguinarine acid salt in a purity of 95 to 100% and containing 0.0 to 5% chelerythrine and/or other benzophenanthridine alkaloids.

In the present invention the alkaloid extract is dissolved into an alcohol or water solvent. The pH is then adjusted to pH 8-10 using any available base. The base form extract is then allowed to stand and precipitate. The precipitate is collected and dried. The precipitate is resuspended in methanol, ethanol or the like. The suspension is heated to selectively improve the alcohol solubility of some of the base forms of the benzophenanthridine alkaloids such as sanguinarine. The suspension is hot filtered. The remaining precipitate is then resuspended in an alcohol and acidified with an mineral or organic acid such as hydrochloric acid, sulfuric acid, nitric acid, gluconic acid, lactic acid, benzoic acid, palmitic acid and the like. The alkaloid is allowed to precipitate and is then collected. This base precipitate procedure results in the recovery of chelerythrine acid salts in a purity of 95 to 100% and contains 0.0 to 5% sanguinarine and/or other benzophenanthridine alkaloids.

Figure 1:
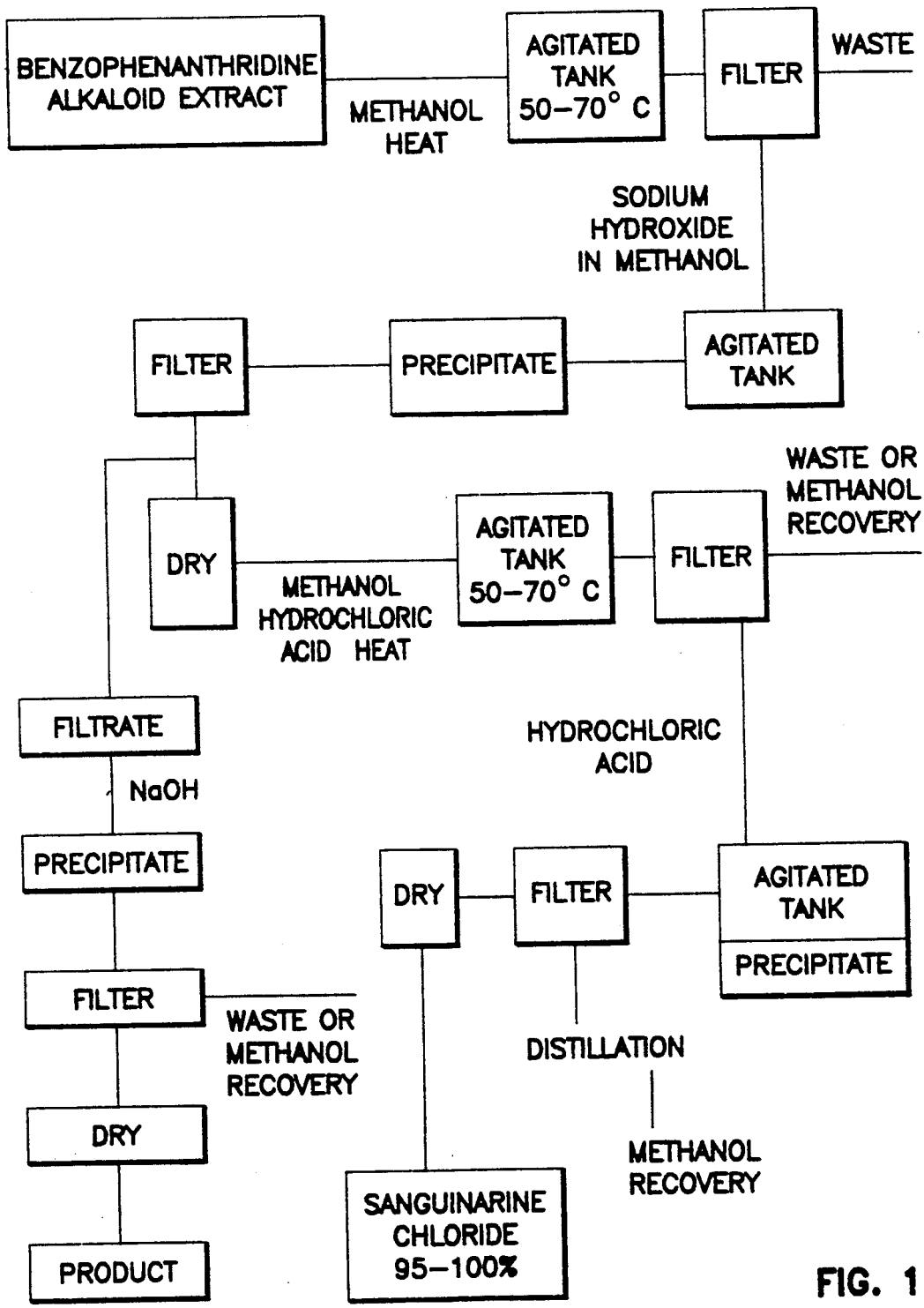
FIG. 1 is a block diagram of the process for purifying sanguinarine from a benzophenanthridine alkaloid extract.

FIG. 1 illustrates the process of the invention for purifying sanguinarine from the alkaloid extract. Alkaloid extract is dissolved in methanol in an agitated tank at a temperature of about 40° to 80° C. (preferably 50°-70° C.) The solution is filtered to remove insolubles. The filtered solution is treated with a known amount of caustic solution to precipitate the sanguinarine as a base form. The precipitate is allowed to form for 16-24 hours. It is collected and dried. The filtrate is then moved to another tank and additional caustic is added to precipitate the remaining alkaloid from the methanol solution. The dried sanguinarine precipitate is suspended in methanol. The appropriate mineral or organic acid is added to reform the sanguinarine iminium ion. The iminium ion will dissolve in the methanol. It is filtered at about 40° to 80° C. (preferably 50°-70° C.) to remove insolubles. Additional acid is added to the hot filtrate and it is allowed to cool for crystallization. The precipitate is collected and dried to obtain the purified sanguinarine chloride.

Figure 2:
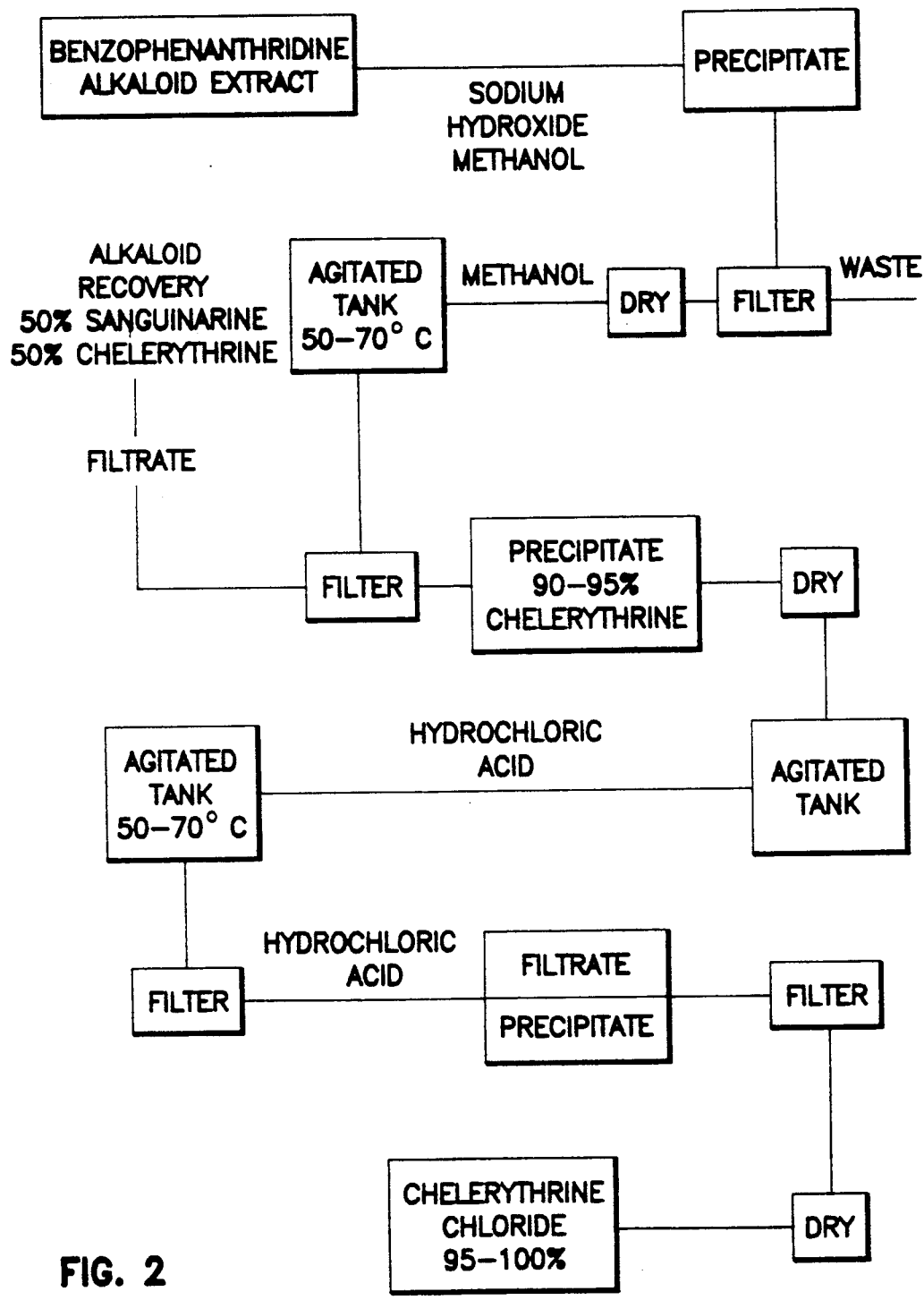
FIG. 2 is a block diagram of the process for purifying chelerythrine from a benzophenanthridine alkaloid extract.

FIG. 2 illustrates the process of the invention for purifying chelerythrine from the alkaloid extract. The alkaloid extract is converted to a base form. The base form is collected by filtration. The base form extract is suspended in methanol in an agitated tank. The suspension is then stirred and can be heated to 40° to 80° C. (preferably 50°-70° C.). The suspension is filtered and the remaining precipitate is resuspended in methanol. A mineral or organic acid is added to the suspension. The solution is heated to 40° to 80° C. (preferably 50°-70° C.) and filtered. Additional acid is added to the filtrate. The solution is allowed to cool and crystallize. The precipitate is collected and dried to obtain the purified chelerythrine chloride or redissolved in hot solvent for recrystallization. The filtrate from the first methanol suspension and filtration contains 50% sanguinarine and 50% chelerythrine. This base form product can be acidified and collected as a precipitate. This precipitate can be used to produce sanguinarine by selective base precipitation as described in FIG. 1.

EXAMPLE 1

A 9.7 gram sample of Macleaya Extract containing 5.7 grams of sanguinarine and 2.9 grams of chelerythrine (total alkaloid 8.6 grams) was dissolved in 388 ml of methanol. The solution was heated to 50° C. and filtered through a CUNO 50S Zeta filter. 2.3 ml of a 50/50 ammonium hydroxide/methanol solution (v/v) was added to the hot filtrate to raise the pH to 6.3.

The filtrate was allowed to cool overnight and precipitate. The precipitate was collected on a Buchner funnel washed with methanol and then dried at 40° C. overnight. The precipitate (6.0 grams) was suspended in 240 ml of methanol after which 1.2 ml of concentrated hydrochloric acid was added. The solution was stirred and heated to 50° C. for fifteen minutes. The solution was filtered through Whatman No. 1 filter paper. The hot filtrate was stirred and an additional 1.2 ml of hydrochloric acid was added. The solution was stirred for an additional fifteen minutes. The heat was removed and the filtrate was allowed to stand overnight. The precipitate formed was collected, dried and analyzed. The yield was 4.8 gram of 97% sanguinarine chloride and 2.7% chelerythrine chloride.

EXAMPLE 2

A 10 gram sample of Macleaya Extract was dissolved in 400 ml of methanol. The methanol solution was heated to 60° C. and filtered through a CUNO 50s filter. 1.6 ml of a 50/50 ammonium hydroxide/methanol solution (v/v) was added to the hot filtrate to raise the pH to 6.5. The filtrate was allowed to cool overnight and precipitate. The precipitate (3.3 grams) was collected, washed with methanol and dried. The precipitate was suspended in 130 ml of methanol and 0.65 ml of concentrated hydrochloric acid was added. The solution was heated to 63° C. and filtered. An additional 0.65 ml of concentrated acid was added to the filtrate. The solution was allowed to stand overnight and crystallize. The precipitate was collected and dried at 40° C. The yield was 2.6 g of 99.4% sanguinarine chloride and 0.6% chelerythrine chloride.

EXAMPLE 3

A 10 gram sample of Macleaya Extract was dissolved in 400 ml of methanol at 57° C. The methanol solution was filtered and 55 ml of a 1% sodium hydroxide in methanol solution (w/v) was added to the hot filtrate to raise the pH to 6.7. The filtrate was allowed to cool for 3 hours to 25° C. The precipitate was collected, washed with methanol and dried overnight at 40° C. The precipitate was suspended in 175 ml of methanol and heated to 55° C. 1.75 ml of concentrated hydrochloric acid was added to the suspension. The solution was filtered hot and allowed to cool overnight. The crystals were collected and dried at 40° C. The yield was 3.5 g of 98.9% sanguinarine chloride and 1.1% of chelerythrine chloride.

EXAMPLE 4

5000 grams of Macleaya Extract containing 51% by weight sanguinarine and 29% by weight chelerythrine was dissolved in 156 liters of methanol. The methanol solution was heated to 59° C. and filtered through a CUNO 50S filter. The hot filtrate was stirred and 27.5 liters of 1% sodium hydroxide was added to the filtrate. The filtrate was allowed to stand overnight and precipitate. The precipitate was collected, washed with methanol and dried under a vacuum of 20 inches mercury at 35° C. overnight. The filtrate was saved for precipitation of alkaloid by raising the pH to 10 with a 20% sodium hydroxide solution. The precipitate (1,914 grams) was suspended in 64 liters of methanol and heated to 55° C. 320 ml of concentrated hydrochloric acid (HCl) was added to the suspension. The solution was filtered through a Whatman No. 1 filter paper. An additional 320 ml of concentrated HCl was added to the filtrate. The filtrate was stirred and allowed to stand overnight for crystallization. The precipitate was collected and dried for 48 hours under a vacuum of 20 inches of mercury at 35° C. The yield was 1,510 grams of 98.8% sanguinarine chloride 1.2% chelerythrine chloride and 0.1% norsanguinarine.

EXAMPLE 5

A 10 gram sample of Sanguinaria Extract containing 40% by weight sanguinarine and 40% other benzophenanthridine alkaloids (chelerythrine, sanguirubine, chelirubine, sanguilutine and chelilutine) was dissolved in 400 ml of methanol and heated to 57° C. The solution was filtered and 11 ml of a 5% sodium hydroxide/methanol (w/v) solution was added to the hot filtrate to raise the pH to 6.6. The filtrate was allowed to cool and precipitate overnight. The precipitate was collected, washed with alcohol and dried at 50° C. The precipitate was suspended in 130 ml of methanol and 0.65 ml of concentrated HCl was added to the suspension. The solution was heated to 60° C. and filtered. An additional 0.65 ml of HCl was added to the hot filtrate. The filtrate was allowed to cool overnight and crystallize. The precipitate was collected and dried at 40° C. The yield was 3.3 g of 96% sanguinarine chloride, 1.1% chelirubine chloride, 0.8% sanguirubine chloride and 1.2% chelerythrine chloride.

The precipitate was dissolved in 110 ml methanol and 0.5 ml of concentrated HCl was added. The solution was heated to 60° C. and filtered. The solution was heated to 60° C. and filtered. The filtrate was cooled and crystallized. The precipitate was collected and dried overnight. The yield was 2.8 grams of 98% sanguinarine chloride, 1.0% chelirubine chloride, and 0.7% chelerythrine chloride.

EXAMPLE 6

A 10 gram sample of Macleaya extract was dissolved in 400 ml of methanol and filtered at 55° C. 55 ml of a 1% NaOH/methanol solution was added to the hot filtrate to raise the pH to 6.5. The filtrate was cooled and precipitated. The precipitate was collected and dried. The precipitate was suspended in 130 ml methanol. A 4 gram sample of benzoic acid in 10 ml methanol was prepared. The suspended precipitate was heated to 50° C. and the benzoic acid/methanol solution was added. The solution was allowed to cool and crystallize. The yield was 3 grams of 97% sanguinarine benzoate and 1.5% chelerythrine benzoate.

EXAMPLE 7

A 10 g sample of benzophenanthridine alkaloid extract containing 35% sanguinarine and 65% chelerythrine in the base form at pH 9 was suspended in 200 ml of methanol. The suspension was stirred and heated to 55° C. The hot suspension was filtered through Whatman No. 541 filter paper. The filtrate was transferred for recovery of an extract containing 55% sanguinarine/45% chelerythrine. The remaining precipitate was resuspended in 200 ml methanol. The suspension was heated to 50° C. and filtered through Whatman No. 541 filter paper. The 6.4 g of precipitate was collected and suspended in 100 ml methanol. 3 ml of concentrated hydrochloric acid was added. The solution was heated to 55° C. and filtered. An additional 3 ml of concentrated hydrochloric and was added to the hot filtrate. The solution was allowed to stand overnight and crystallize. The precipitate was collected and dried at 40° C. The yield was 4.8 g of 98% chelerythrine chloride and 2.0% sanguinarine chloride.

EXAMPLE 8

A 5 g sample of benzophenanthridine alkaloid extract containing 20% sanguinarine and 80% chelerythrine in the base form at pH 9.2 was suspended in 100 ml of methanol. The suspension was stirred and heated to 50° C. The hot suspension was filtered through Whatman No. 1 filter paper. The filtrate was transferred for later recovery of an extract containing 53% sanguinarine and 47% chelerythrine. The remaining precipitate was resuspended in 100 ml methanol and heated to 50° C. The suspension was hot filtered through Whatman No. 2 filter paper. The 3.0 g of precipitate was collected and suspended in 50 ml of methanol. 2 ml of concentrated hydrochloric acid was added. The solution was heated to 50° C. and allowed to cool and crystallize. The yield was 2.7 g of 99% chelerythrine chloride and 0.5% sanguinarine chloride.

EXAMPLE 9

A 10 g sample of benzophenanthridine alkaloid extract in the base form at pH 9.6 containing 34% sanguinarine/66% chelerythrine was suspended in 100 ml of ethanol. The suspension was stirred at room temperature. The suspension was filtered through Whatman No. 541 filter paper. The remaining precipitate was resuspended 5 more time in 100 ml ethanol and stirred at room temperature. The 4.3 g of precipitate remaining was collected and suspended in 50 ml of methanol. 3 ml of concentrated hydrochloric acid was added. The solution was heated to 50° C. and allowed to cool and crystallize. The yield was 3.9 g of 96% chelerythrine chloride with 1.2% sanguinarine chloride.

What is claimed is:

1. A process for separating sanguinarine from an isolated mixture of sanguinarine and another benzophenanthridine alkaloid selected from the group consisting of chelerythrine sanguirubine, chelirubine, sanguilutine, chelilutine and combinations thereof, which comprises:

dissolving the mixture in a C1–C5 alcoholic or aqueous solvent to form a crude solution;

adjusting the pH of the crude solution to a value of about 5.5 to about 7 to form a precipitate and a remaining solution;

separating the precipitate from the remaining solution;

dissolving the precipitate in an acidic C1–C5 alcohol solvent at a temperature between ambient to about the boiling point of the alcohol to form a refined solution, the weight percent of acid in the acidic alcohol solvent relative to the weight of the alcohol being 0.1 to 75%;

cooling the refined solution to crystallize sanguinarine acid salt having a purity of at least about 95%.

2. A process according to claim 1 wherein the mixture essentially is sanguinarine and chelerythrine.

3. A process according to claim 1 wherein the acidic alcoholic solvent contains an acid selected from the group consisting of hydrochloric acid, sulfuric acid, nitric acid, acetic acid, lactic acid, gluconic acid, benzoic acid, palmitic acid, citric acid and tartaric acid.

4. A process according to claim 1 wherein the pH is adjusted with a base selected from the group consisting of ammonium hydroxide, sodium hydroxide, sodium carbonate, potassium hydroxide and sodium hydride.

5. A process according to claim 1 wherein the alcohol is selected from the group consisting of methanol, ethanol, isopropanol, 1-propanol, butanol and pentanol.

6. A process for separating chelerythrine from an isolated mixture of chelerythrine and a benzophenanthridine alkaloid selected from the group consisting of sanguinarine sanguirubine, chelirubine, sanguilutine, chelilutine and any combination thereof, which comprises;

dissolving the mixture in a C1–C5 alcoholic or aqueous solvent to form a crude solution;

adjusting the pH of crude solution to a value of about 8 to about 10 to form a precipitate and a remaining solution;

separating the precipitate and the remaining solution;

suspending the precipitate in hot alcohol at a weight ratio of precipitate to alcohol of no more than about 2:5, the alcohol being at a temperature of from about 40° to 80° C.;

separating the alcohol treated precipitate from the hot alcohol;

dissolving the alcohol treated precipitate in acidic alcohol solvent at a temperature of from about 40° to 80° C. to form a refined solution, the weight percent of acid in the acidic alcohol solvent relative to the weight of alcohol being 0.1 to 75%;

cooling the refined solution to crystallize chelerythrine acid salt having a purity of at least about 95%.

7. A process according to claim 6 wherein the mixture essentially is sanguinarine and chelerythrine.

8. A process according to claim 6 wherein the acidic alcoholic solvent contains an acid selected from the group consisting of hydrochloric acid, sulfuric acid, nitric acid, acetic acid, lactic acid, gluconic acid, benzoic acid, palmitic acid, citric acid and tartaric acid.

9. A process according to claim 6 wherein the pH is adjusted with a base selected from the group consisting of ammonium hydroxide, sodium hydroxide, sodium carbonate, potassium hydroxide and sodium hydride.

10. A process according to claim 6 wherein the alcohol is selected from the group consisting of methanol, ethanol, isopropanol, 1-propanol, butanol and pentanol.

* * * * *

UNITED STATES PATENT AND TRADEMARK OFFICE
CERTIFICATE OF CORRECTION

PATENT NO.   :   5,133,981

DATED        :   July 28, 1992

INVENTOR(S)  :   Harkrader et al.

It is certified that error appears in the above-identified patent and that said Letters Patent is hereby corrected as shown below:

```
On the title page:
```
At [54], please delete "EXTRACTS" first instance.

Signed and Sealed this

Twenty-fifth Day of July, 1995

Attest:

BRUCE LEHMAN

*Attesting Officer*   Commissioner of Patents and Trademarks